US008163897B2

(12) United States Patent
Kore et al.

(10) Patent No.: US 8,163,897 B2
(45) Date of Patent: Apr. 24, 2012

(54) 5-BROMO-2'-DEOXY-URIDINE LABELED NUCLEOTIDE TRIPHOSPHATES AND NUCLEIC ACID PROBES AND METHODS OF MAKING AND USING THE SAME

(75) Inventors: Anilkumar R. Kore, Austin, TX (US); Zhongting Hu, Los Angeles, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/038,184

(22) Filed: Mar. 1, 2011

(65) Prior Publication Data

US 2011/0207920 A1    Aug. 25, 2011

(51) Int. Cl.
 *C07H 21/00* (2006.01)
 *C12Q 1/68* (2006.01)
 *C07H 21/02* (2006.01)
 *C12P 19/34* (2006.01)
 *B01L 3/00* (2006.01)

(52) U.S. Cl. .................. 536/25.3; 536/23.1; 536/24.3; 435/6; 435/91.1; 422/61

(58) Field of Classification Search ................. 536/23.1, 536/24.3, 25.3; 435/6, 91.1; 422/61
See application file for complete search history.

(56) References Cited

U.S. PATENT DOCUMENTS 6,887,690 B2  5/2005  Fisher et al.
7,915,392 B2  3/2011  Kore et al.

FOREIGN PATENT DOCUMENTS

WO   WO2008/157311   12/2008

OTHER PUBLICATIONS

Ausubel et al., "Current Protocols in Molecular Biology," vol. 2, Chapter 14, In Situ Hybridization and Immunohistochemistry. 2008.
Browning et al., "Studies on the differing effects of tumor necrosis and lymphotoxin on the growth of several human tumor lines," Journal of Immunology, vol. 142, No. 6, Sep. 15, 1989,1859-1867.
Dundr et al., "Nonisotopic ultrastructural mapping of transcription sites within the nucleolus," Experimental Cell Research, vol. 208, No. 1, Sep. 1993, 275-281.
Farries et al., "Biosynthesis of Properdin," Journal of Immunology, vol. 142, No. 3, Feb. 1, 1989, 842-847.
Jung et al., "Crosslinking of platelet glycoprotein 1b by N-succinimildyl (4- azidophenyldithio)propionate and 3,3'-dithiobis-(sulfosuccinimidyl propionate)," Biochimica et Biophysica Acta (BBA)—General Subjects, vol. 761, Issue 2, Dec. 13, 1983, 152-162.
Ma et al., "In vitro mutagenesis of xanthomonas campestris α-amylase gene by partially replacing deoxythymidine triphosphate with 5-bromo-2'-deoxyuridine-5'- triphosphate using a PCR technique," Biotechnology Letters, vol. 26, No. 2, Jan. 2004, 171-175.

(Continued)

*Primary Examiner* — Jezia Riley

(57) ABSTRACT

5-bromo-2'-deoxy-uridine (BrdU) labeled nucleotide triphosphates and nucleic acid probes are described herein. The BrdU labeled nucleotide triphosphates include a linker between the nucleotide triphosphate and the BrdU moiety. The linker can be cleavable or non-cleavable. The nucleotide triphosphates can be a ribonucleotide triphosphates, 2'-deoxyribonucleotide triphosphates or 2',3'-dideoxyribonucleotide triphosphates. The nucleic acid probes can be used for in situ hybridization.

5 Claims, 2 Drawing Sheets

OTHER PUBLICATIONS

Millar et al., "Chronic desensitization to bombesin by progressive down-regulation of bombesin receptors in Swiss 3T3 cells. Distinction from acute desensitization", The Journal of Biological Chemistry, vol. 265, No. 20, Jul. 15, 1990 12052-12058.

Murakami et al., "Fluorescent-labeled oligonucleotide probes: detection of hybrid formation in solution by fluorescence polarization spectroscopy," Nucleic Acids Research, vol. 19, Issue 15, Aug. 11, 1991, 4097-4102.

Park et al., "Characterization of the cell surface receptor for a multi-lineage colonystimulating factor (CSF-2 alpha)", The Journal of Biological Chemistry, vol. 261, No. 1, Jan. 5, 1986, 205-210.

Roche Applied Science, "DIG RNA Labeling Kit (SP6/T7): RNA labeling with digoxigenin-UTP by in vitro transcription with SP6 and T7 RNA polymerase," Catalog No. 11 175 025 910, Kit for 2x 10 labeling reactions, 1-6, 2006.

Stanek, et al., "Pre-ribosomal RNA is processed in permeabilised cells at the site of transcription," European Journal of Cell Biology, vol. 79, Issue 3, Mar. 2000, 202-207.

Tanaka et al., Syringe method for stepwise chemical synthesis of oligonucleotides, Nucleic Acid Research, vol. 10, Issue 10, May 25, 1982, 3249-3259.

Thevenin, et al., Biophysical Journal, vol. 59, 1991, 358a.

5-BROMO-2'-DEOXY-URIDINE LABELED NUCLEOTIDE TRIPHOSPHATES AND NUCLEIC ACID PROBES AND METHODS OF MAKING AND USING THE SAME

This application claims priority to U.S. patent application Ser. No. 12/138,673 filed Jun. 13, 2008, issued as U.S. Pat. No. 7,915,392 which application claims the benefit of U.S. Provisional Application Ser. No. 60/929,130, filed Jun. 14, 2007, the disclosures of which are specifically incorporated herein by reference in their entirety.

The section headings used herein are for organizational purposes only and should not be construed as limiting the subject matter described herein in any way.

FIELD

This application relates generally to nucleic acid probes for conducting biological assays and to methods of making and using said probes as well as to compounds related thereto.

INTRODUCTION

In situ hybridization (ISH) uses a labeled complementary DNA or RNA strand (i.e., a probe) in the determination of a specific DNA or RNA sequence in a tissue sample. In contrast to other methods, ISH enables the morphological demonstration of specific DNA or RNA sequences in individual cells, tissue sections, single cells, or chromosome preparations. Hence, ISH can be used to determine DNA and RNA sequences in a heterogeneous cell population, and to determine if a gene is expressed in low levels in all of the cells or in high levels in only a few of the cells.

Although isotopic in situ hybridization is the most sensitive method to detect intracellular mRNA distribution, non-isopotic in situ is a much safer and quicker technique to localize mRNA. The ISH procedure typically ranges from two to four days for non-isotopic in situ compared and can be significantly longer for isotopic in situ hybridization.

SUMMARY

A compound is provided which is represented by the formula:

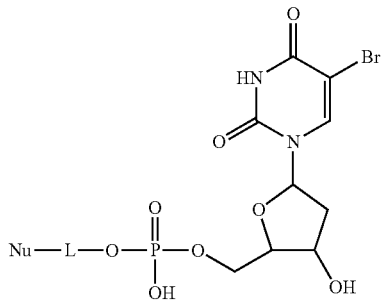

wherein "Nu" is a nucleotide triphosphate, a 2'-deoxynucleotide triphosphate or a 2',3'-dideoxynucleotide triphosphate and wherein L is a linker group. A salt of this compound (e.g., a sodium salt) is also provided.

A polynucleotide is also provided which is represented by the formula:

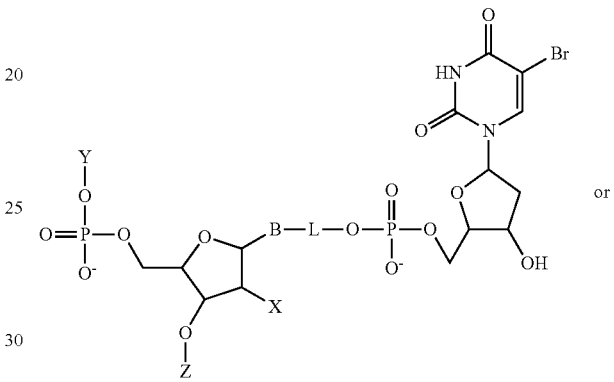

or

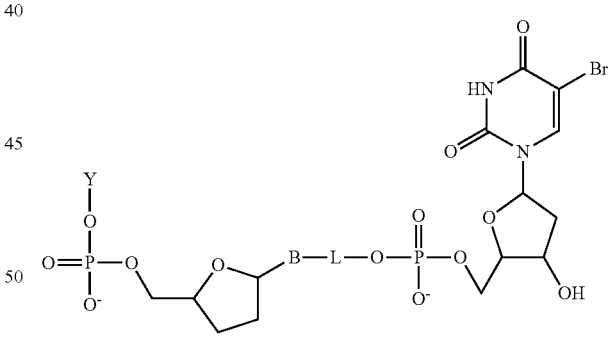

wherein "Y" is a nucleoside, a nucleotide or a polynucleotide, "Z" is H, a nucleotide or a polynucleotide, "X" is H or OH, "B" is a nucleobase and "L" is a linker group.

A polynucleotide is also provided which is represented by the formula:

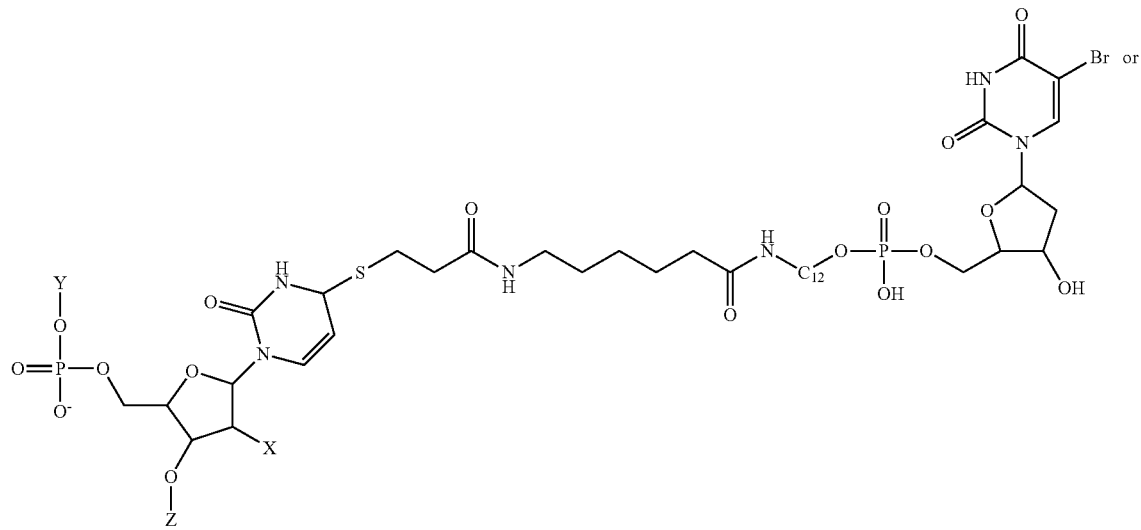

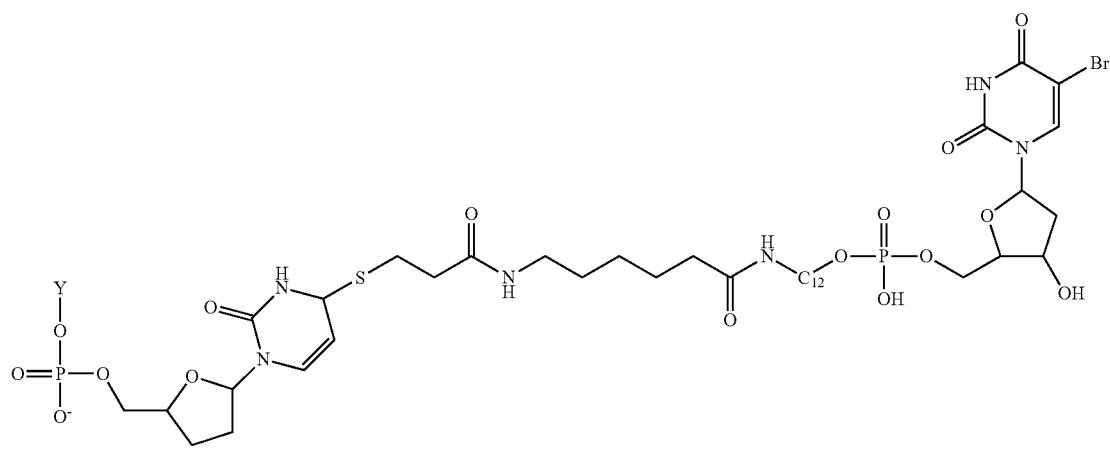

wherein "Y" is a nucleoside, a nucleotide or a polynucleotide, "Z" is H, a nucleotide or a polynucleotide and "X" is H or OH.

A method for detecting the presence of a nucleic acid analyte in a tissue sample is also provided which comprises:

incubating the tissue sample with a composition comprising a polynucleotide as set forth above, wherein the polynucleotide binds to the nucleic acid analyte;

washing the sample;

contacting the sample with an anti-BrdU antibody conjugated to a detectable moiety or to an enzyme; and detecting the detectable moiety or enzyme.

A composition is also provided which comprises: adenosine triphosphate (ATP); uridine triphosphate (UTP); guanosine triphosphate (GTP); cytidine triphosphate (CTP); and a compound of the formula:

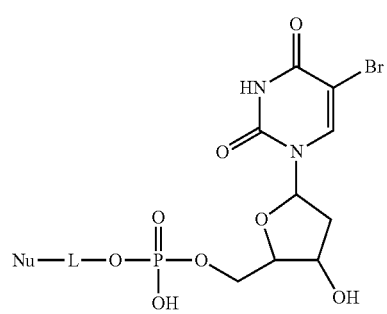

or a salt thereof, wherein "Nu" is a ribonucleotide triphosphate and wherein L is a linker group. A kit is also provided which comprises a composition as set forth above and an RNA polymerase.

A composition is also provided which comprises dATP, dCTP, dGTP, dTTP and a compound of the formula:

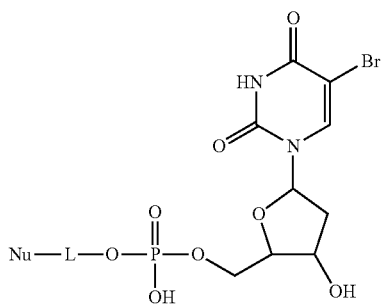

or a salt thereof, wherein "Nu" is a 2'-deoxyribonucleotide triphosphate or a 2',3'-dideoxyribonucleotide triphosphate and wherein L is a linker group. A kit is also provided which comprises a composition as set forth as set forth above and a DNA polymerase or terminal transferase.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF THE VARIOUS EMBODIMENTS

Figure 1:
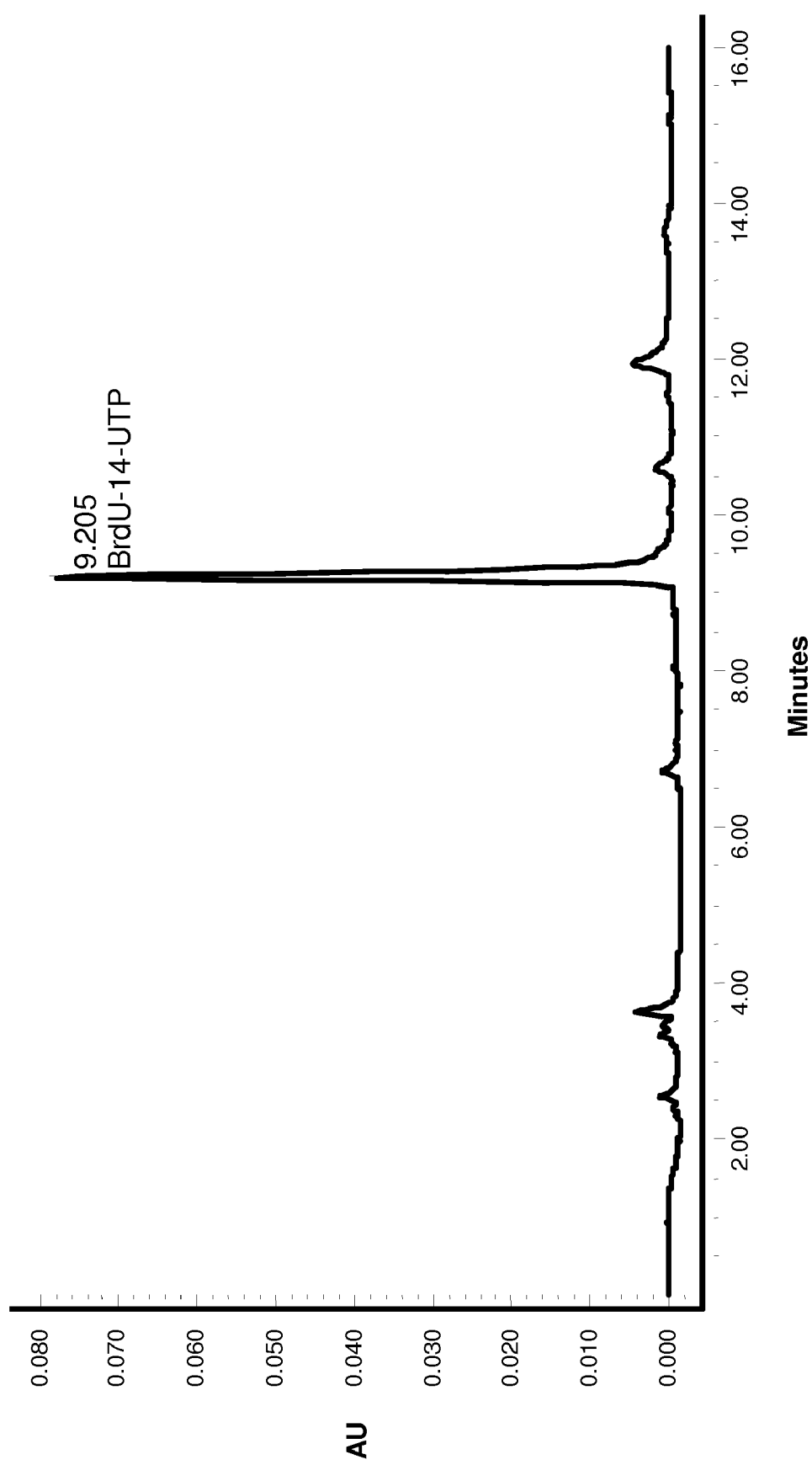
FIG. 1 is an HPLC Profile of a 5-bromo-2'-deoxy-uridine (BrdU) labeled uridine triphosphate (UTP) probe.

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of"

As used herein, the term "nucleobase" refers to a nitrogen containing heterocyclic moiety capable of forming Watson-Crick hydrogen bonds in pairing with a complementary nucleobase. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine).

As used herein, the term "nucleoside" refers to a compound consisting of a nucleobase linked to the C-1' carbon of a ribose sugar. The ribose may be substituted or unsubstituted. Exemplary ribose sugars include ribose, 2'-deoxyribose and 2',3'-dideoxyribose (also referred to herein as dideoxyribose).

As used herein, the term "nucleotide" refers to a phosphate ester of a nucleoside as a monomer unit or within a polynucleotide.

As used herein, the term "nucleotide triphosphate" refers to a nucleotide with a triphosphate ester group at the 5' position.

As used herein, the terms "polynucleotide", "oligonucleotide" and "nucleic acid' are used interchangeably and refer to single stranded and double stranded polymers of nucleotide monomers, including ribonucleotides (RNA) and 2'-deoxyribonucleotides (DNA) linked by internucleotide phosphodiester bond linkages. A polynucleotide may be composed entirely of deoxyribonucleotides, entirely of ribonucleotides or chimeric mixtures thereof.

As used herein, the term "salt" refers to a salt of a compound or a mixture of salts of a compound. For example, the salt can be a sodium salt, or a mixture of the sodium and potassium salts of the compound. In addition, zwitterionic forms of a compound are also included in the term "salt." Salts of acidic functional groups (e.g. a phosphate group) may have a countercation, such as sodium, potassium, magnesium, calcium, etc.

As used herein, the term "hydroxyl protecting group" refers to any hydroxyl protecting group that is compatible with oligonucleotide synthesis. For a detailed description of nucleic acid synthesis methodology, and hydroxyl protecting groups that can be used therein, please see: Gait, Oligonucleotide Synthesis: A Practical Approach, IRL Press, Oxford England. Other suitable hydroxyl protecting groups can be found in: Green et al., Protecting Groups In Organic Synthesis, Third Edition, John Wiley & Sons, Inc. New York, 1999).

As used herein, the terms "linker", "linker group" and "linking group" are used interchangeably and refer to any chemical group (e.g. $R_1$ and $R_2$) that connects two or more other chemical groups. Linking groups can be substituted or unsubstituted alkyl, alkeneyl or alkynyl groups, which may optionally comprise one or more heteroatoms (substituted for a carbon atom), such as oxygen, sulfur, nitrogen or silicon, in the chain as well as one or more unsaturated carbon-carbon bonds. For example, the linking group may comprise one or more disulfide, amide and/or ester bonds. For example, a linking group can be: a) a $C_{1-10}$ alkyl group, b) a $C_{2-10}$ alkenyl group, c) a $C_{2-10}$ alkynyl group, d) a $C_{3-14}$ cycloalkyl group, e) a $C_{6-14}$ aryl group, f) a $C_{1-10}$ heteroalkyl group, g) a $C_{2-10}$ heteroalkenyl group, h) a $C_{2-10}$ heteroalkynyl group, i) a 3-14 membered cycloheteroalkyl group, or j) a 5-14 membered heteroaryl group wherein each of a)-j) optionally is substituted with one or more independently selected $R_6$ groups, wherein $R_6$ is halogen, —CN, —$NO_2$, OXO, —OH, —$OR_7$, —$NH_2$, —$NHR_7$, —$N(R_7)_2$, or a $C_{1-10}$ alkyl group, wherein $R_7$ is a substituted or unsubstituted $C_{1-10}$ alkyl group. For example, the linking group can comprise one or more diol and one or more amide bonds as well as one or more unsaturated carbon-carbon bonds. In some embodiments, the linker can comprise one or more amide and one or more ester bonds as well as one or more unsaturated carbon-carbon bonds.

Provided herein is a compound of the formula:

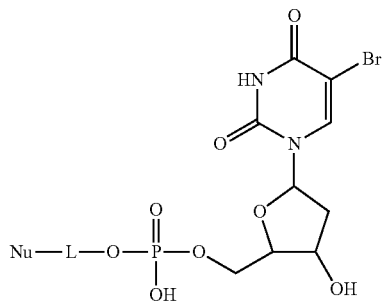

wherein "Nu" is a nucleotide triphosphate, a 2' deoxynucleotide triphosphate or a dideoxy nucleotide triphosphate and wherein L is a linker. A salt of the above compound (e.g., a sodium salt) is also provided.

According to some embodiments, "Nu" in the above formula is a uridine triphosphate, a 2'-deoxyuridine triphosphate or a 2',3'-dideoxyuridine triphosphate. In some embodiments, the compound is of the formula:

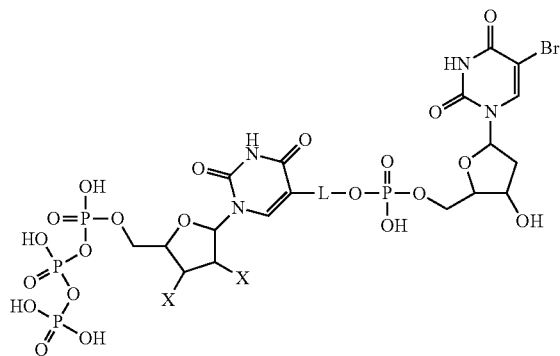

wherein each X in the above formula is independently H or OH and "L" is a linker group. A salt of the above compound (e.g., a sodium salt) is also provided.

According to some embodiments, "L" in either of the above formulae is a cleavable or a non-cleavable linker. Exemplary non-cleavable linkers include, but are not limited to, the following:

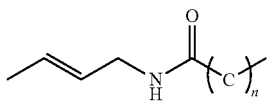

wherein n is an integer greater than 6 (e.g., n=6-12 inclusive).

Exemplary cleavable linker groups include, but are not limited to, the following:

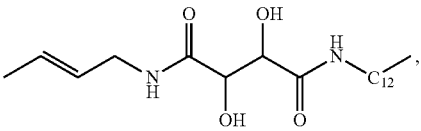

which is cleavable using a mild oxidizing agent;

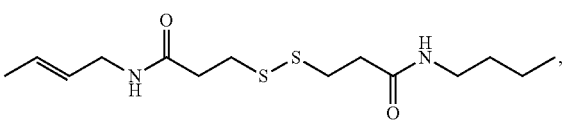

which is a thiol cleavable linker;

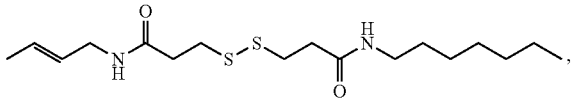

which is a thiol cleavable linker with a longer carbon chain;

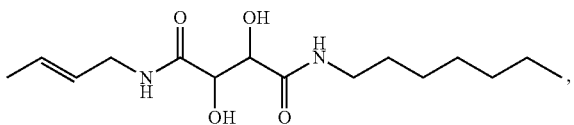

which is cleavable by an oxidizing agent;

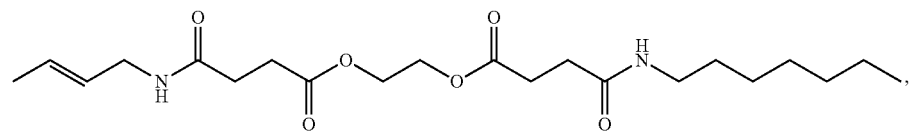

which is cleavable under gentle conditions, such as by using a pH of 8.5 and hydroxyl amine; and

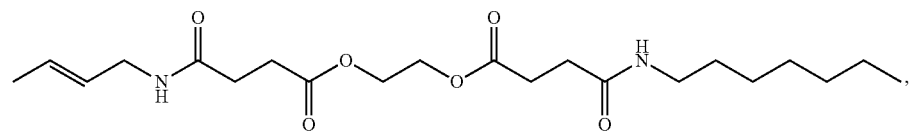

which is water soluble and cleavable using hydroxyl amine. Cleavable linkers are disclosed in: Thevenin et al., Biophysics. J., 59, 358a (1991); Jung et al., Biochim. Biophys. Acta, 761, 152-162 (1983); Farries et al., J. Immunol., 142, 842-847 (1989); Park et al., J. Biol. Chem., 261, 205-210 (1986); Millar et al., J. Biol. Chem., 265, 12052-12058 (1990); and Browning et al., J. Immunol., 143, 1859-1867 (1989).

In some embodiments, the compound has the formula:

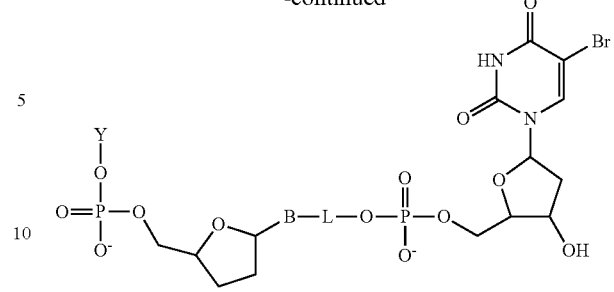

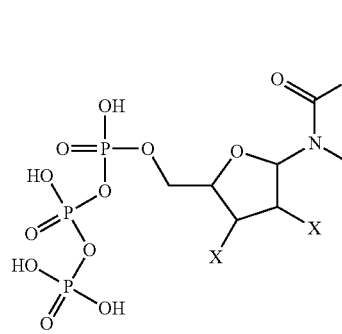

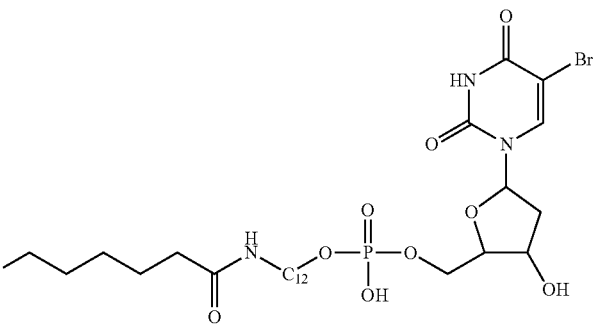

wherein each X is independently H or OH is also provided. A salt of the above compound (e.g., a sodium salt) is also provided.

A BrdU labeled nucleotide as described above can be used to synthesize a polynucleotide probe. The polynucleotide probe can be synthesized by polymerase extension in the presence of a template, an appropriate polymerase and other reagents (e.g. nucleotide triphosphates, magnesium, etc.) and conditions commonly applied to polymerase extension reaction. One of skill in the art would be familiar with the reagents and conditions used to perform a polymerase extension reaction (see, for example, Ma et al., In Vitro Mutagenesis of *Xanthomonas Campestris* α-Amylase Gene by Partially Replacing Deoxythymidine Triphosphate with 5-Bromo-2′-Deoxyuridine-5′-Triphosphate Using a PCR technique, Biotechnology Letters, Vol. 26, No. 2, pp. 171-175(5), (January 2004).

Accordingly, a polynucleotide is also provided which is represented by the formula:

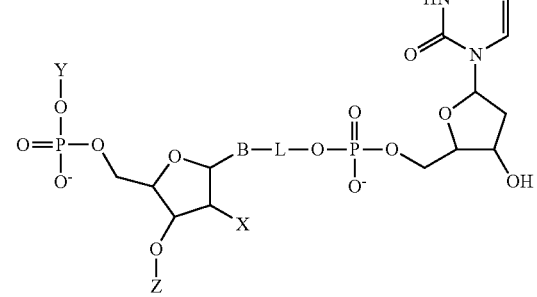

wherein "Y" is a nucleoside, a nucleotide or a polynucleotide, "Z" is H, a nucleotide or a polynucleotide, "X" is H or OH, "B" is a nucleobase and "L" is a linker group.

According to some embodiments, "B" in the above formula is a uracil group and the polynucleotide is represented by the formula:

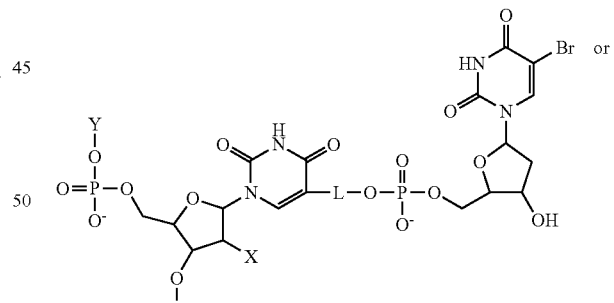

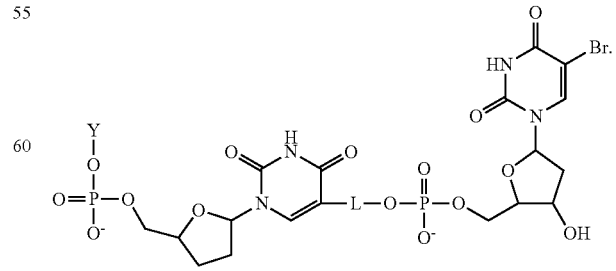

wherein "X", "Z", "L" and "Y" are defined as set forth above.

The polynucleotide can be used as a probe for conducting in situ hybridization assays.

As set forth above, a 5-bromo-2'-deoxy-uridine (BrdU) molecule can be linked to a ribonucleotide triphosphate such as ribo uridine triphosphate (rUTP). The structure of a BrdU-rUTP (designated BrdU-14-UTP) is set forth below:

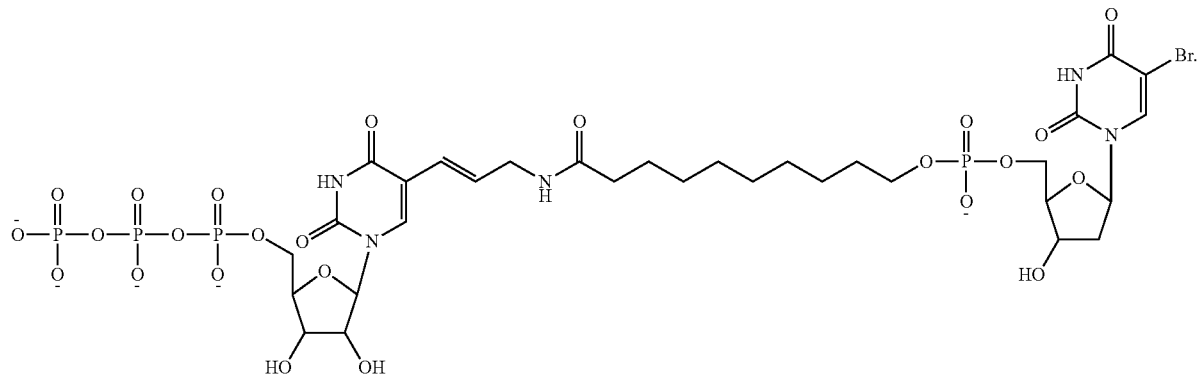

In this probe, 5-BrdU is coupled to a 5-(3-aminoallyl)uridine 5'-triphosphate via a linker group having a 14 atom main chain. This ribo-derivative can be used for synthesizing BrdU-labeled RNA probes with RNA polymerases. When BrdU-UTP is used to generate an antisense probe, BrdU molecules will not anneal to nucleotide A in the sense probe. Therefore, the BrdU antibody can easily recognize and bind to BrdU moieties in the probe. The bound BrdU antibodies can also be easily detected (e.g., by alkaline-phosphatase). The probes can be used for both section in situ or whole-mount in situ assays.

A 5-bromo-2'-deoxyuridine (BrdU) molecule can also be linked to a 2'-deoxy nucleotide triphosphate such as 2'-deoxy uridine triphosphate (dUTP). The structure of BrdU-dUTP (designated BrdU-14-dUTP) is set forth below:

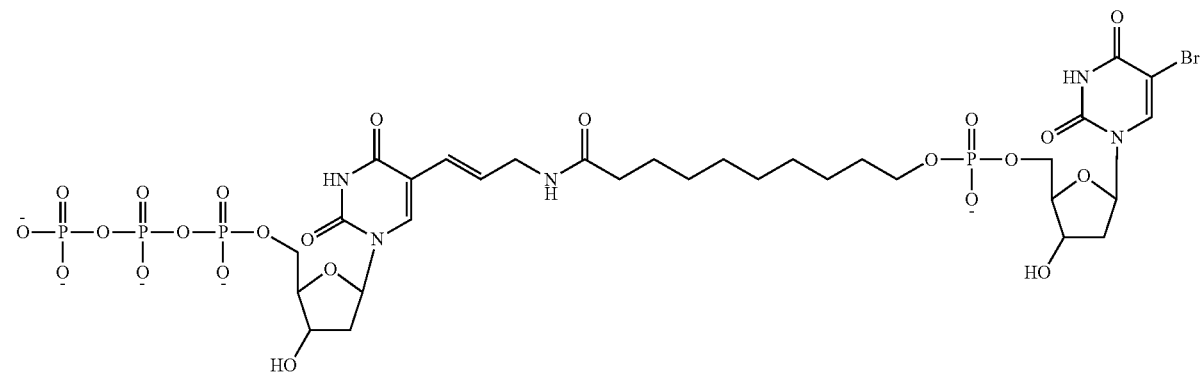

In the above probe, 5-BrdU is coupled to a 5-[3-aminoallyl] 2'-deoxyuridine 5'-triphosphate via a linker group having a 14 atom main chain. The 2'-deoxy probe (i.e. dUTP) can be used for to synthesize BrdU-labeled DNA probes using DNA polymerases.

A 5-bromo-2'-deoxy-uridine (BrdU) molecule can also be linked to a 2',3'-dideoxy nucleotide triphosphate such as 2',3'-dideoxy uridine triphosphate (ddUTP). The structure of a BrdU-ddUTP probe is set forth below:

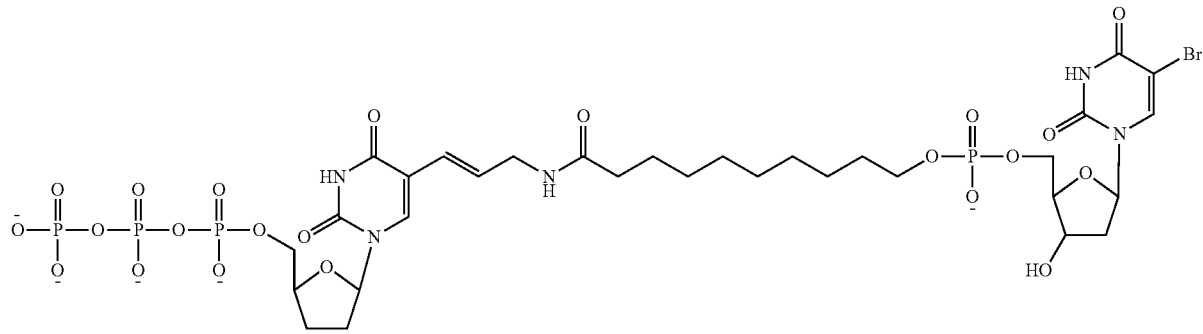

The ddUTP-BrdU probe can be used for 3' end labeling of oligonucleotides with terminal transferase.

The BrdU labeled probes described herein are non-radioactive (i.e., non-isotopic) probes. Therefore, the disadvantages of working with radio isotopes, which include the need for special laboratories, safety measurements/shielding against exposure to radioactivity, special training of people working with radioactivity, expensive waste disposal, and very unstable probes can be avoided.

A general reaction scheme for the synthesis of ribonucleotide-BrdU, 2'-deoxyribonucleotide-BrdU and 2',3'-dideoxyribonucleotide-BrdU probes is set forth below.

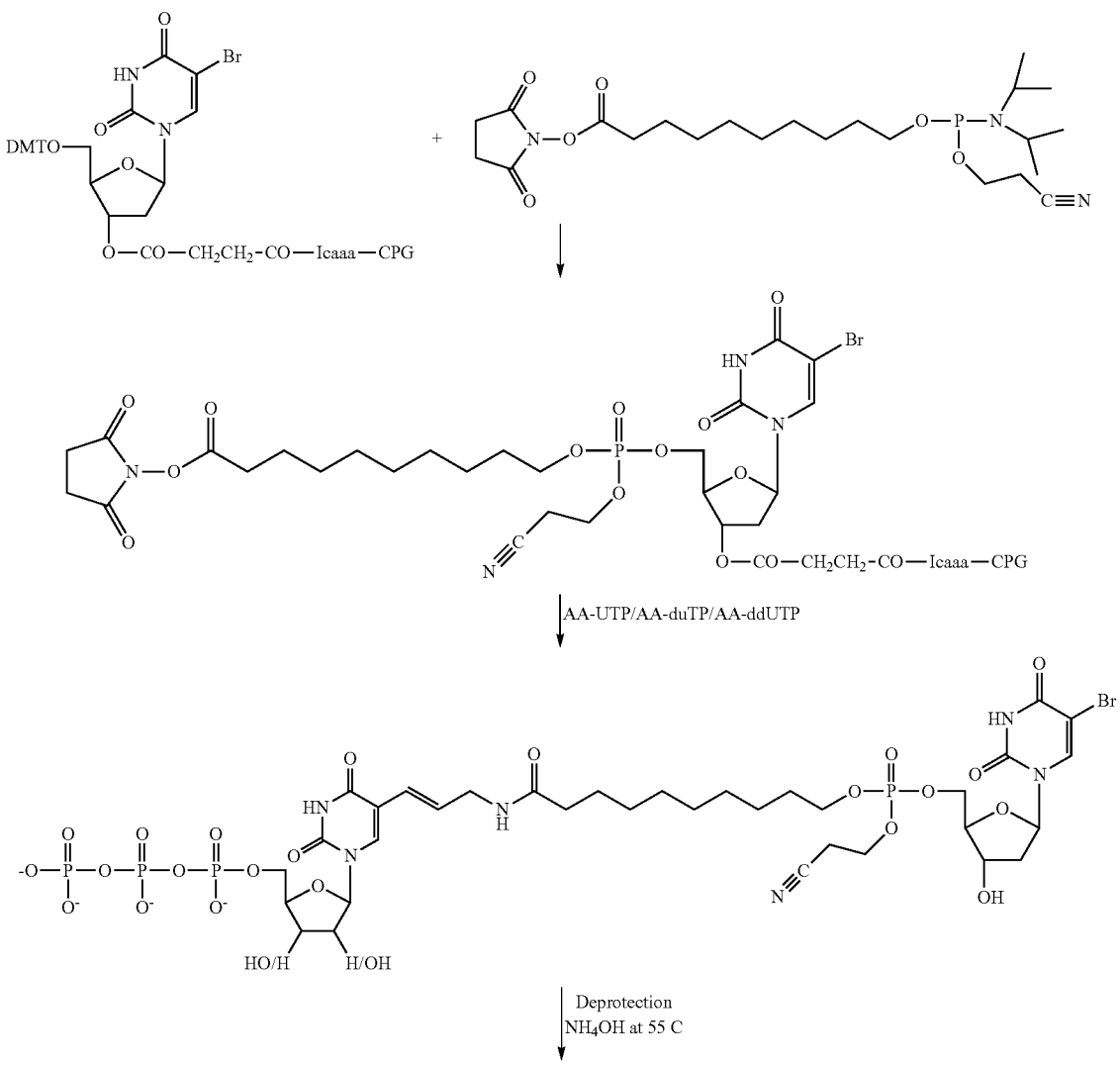

-continued

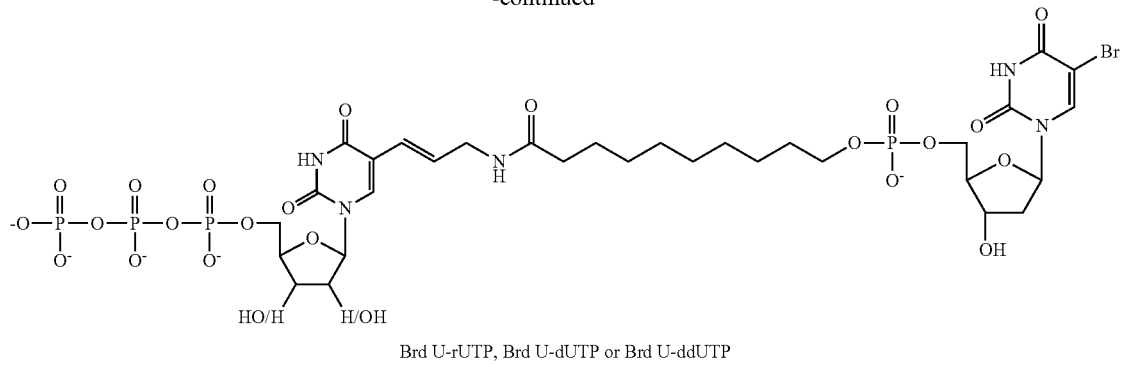

Brd U-rUTP, Brd U-dUTP or Brd U-ddUTP

In the above reaction scheme, "AA-UTP" denotes 5-[3-aminoallyl] uridine 5'-triphosphate", AA-dUTP" denotes 5-[3-aminoallyl] 2'-deoxyuridine 5'-triphosphate", AA-ddUTP" denotes 5-[3-aminoallyl] 2',3'-dideoxyuridine 5'-triphosphate", "lcaa" denotes a long chain amino acid, "CPG" denotes a controlled pore glass support, and "DMT" denotes a dimethoxytrityl group. The designation "H/OH" indicates that either an H or an OH group can be present. Although a controlled pore glass (CPG) support is depicted in the above reaction scheme, other supports can also be used (such supports would be well-known to those skilled in the area of DNA synthesis). In addition, although a dimethoxytrityl group is depicted in the above reaction scheme, other hydroxyl protecting groups could also be used. Such protecting groups would also be well-known to those skilled in the area of DNA synthesis.

Moreover, a method is provided which comprises reacting a compound (1) which is bound to a support:

(1)

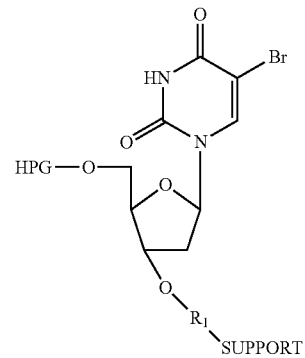

wherein "$R_1$" is a group (i.e. a linking group) linking the nucleoside moiety to the support (denoted "SUPPORT", which could, for example, be CPG) and "HPG" is a hydroxyl protecting group, with the compound (2):

(2)

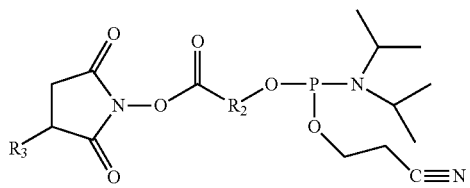

wherein $R_2$ is a linking group, and $R_3$ is H or $SO_3^-$, to form a compound (3):

(3)

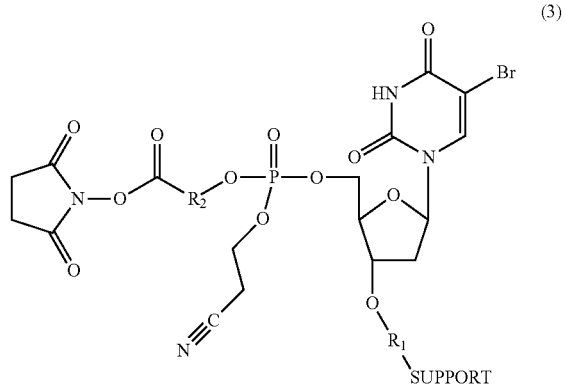

reacting the compound (3) with the compound (4):

(4)

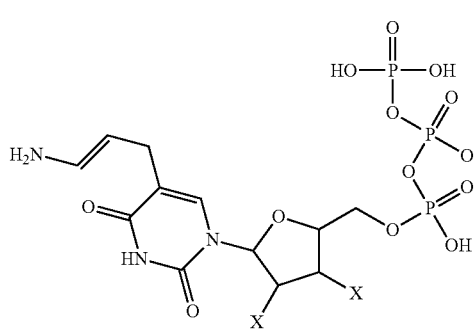

wherein each X is independently H or OH, to form a compound (5);

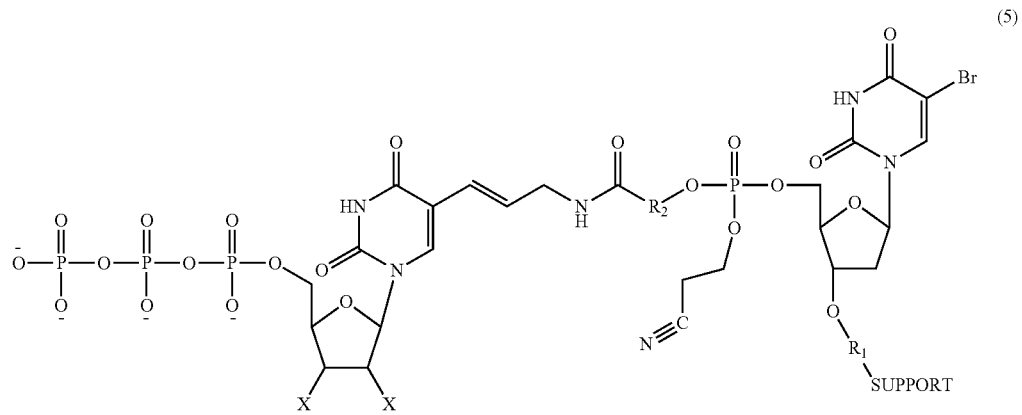

(5)

and removing the compound (5) from the support to form a compound (6);

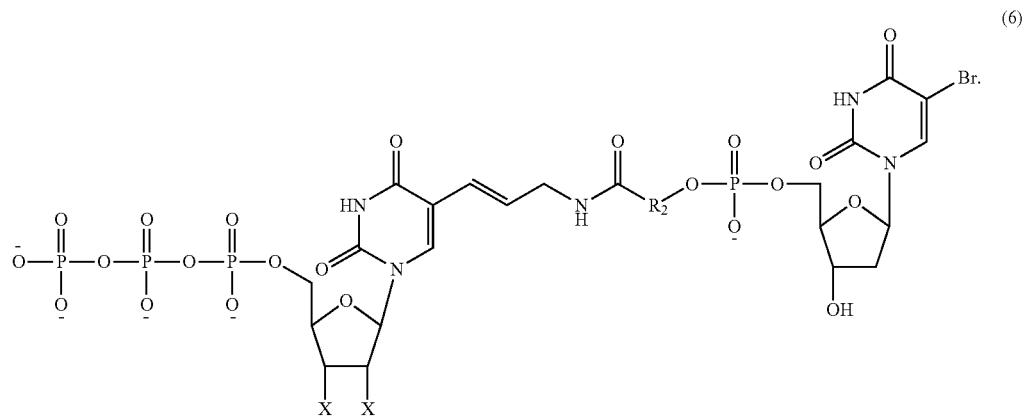

(6)

As set forth in the above method, the BrdU labeled ribonucleotide, 2'-deoxyribonucleotide or dideoxyribonucleotide probes can be made by a method comprising reacting the compound (2):

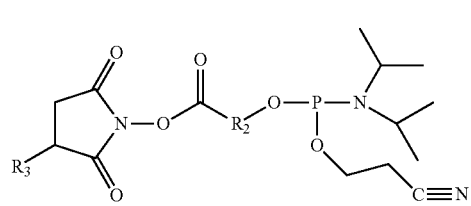

(2)

with a support bound BrdU moiety. In the compound (2), $R_2$ is a linking group, and $R_3$ is H or $SO_3^-$. Exemplary $R_2$ groups include non-cleavable linking groups and cleavable linking groups. Exemplary non-cleavable linking groups that can be used for $R_2$ include, but are not limited to, the following:

wherein n is an integer of at least 6 (e.g., n=6-12).

As set forth above, a linker which can be cleaved (e.g., under mild conditions) can also be used. Exemplary cleavable linking groups include, but are not limited to:

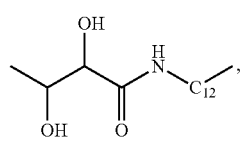

which is cleavable using a mild oxidizing agent;

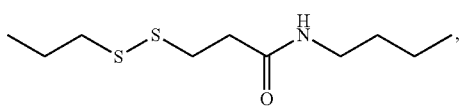

which is thiol-cleavable;

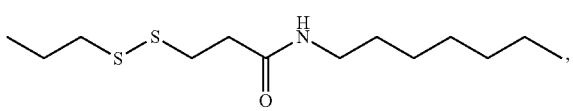

which is thiol-cleavable and which has a longer carbon chain;

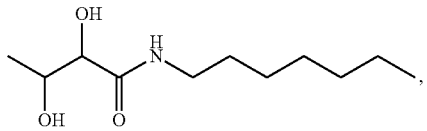

which is cleavable by an oxidizing agent;

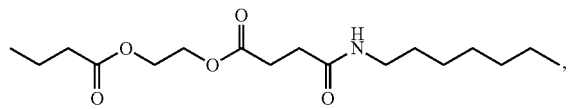

which is cleavable under gentle conditions at pH of 8.5 using hydroxylamine; and

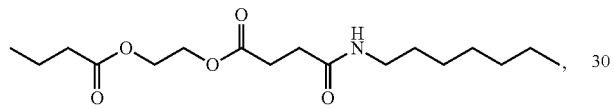

which is water soluble and cleavable using hydroxylamine.

The length of the linking group between the BrdU label and the amino allyl modified ribonucleotide, 2'-deoxyribonucleotide or 2',3'-dideoxyribonucleotide (e.g., AA-rUTP, AA-dUTP or AA-ddUTP) can be varied. According to some embodiments, the length of the linker group can be at least as long as an 11 carbon atom chain. It is to be understood that the linker group can include atoms other than carbon (e.g. sulfur, oxygen, nitrogen or silicon) but without regard to its composition, will have a length that is at least as long as an 11 atom carbon chain. The length of the linker group can be varied to provide a high level of sensitivity during detection. Moreover, a linker group can be used which allows the BrdU moiety to project out far enough from the labeled probe to be efficiently recognized by the antibody during detection.

A method for detecting the presence of a nucleic acid analyte in a tissue sample is also described herein. The method comprises:

incubating the tissue sample with a composition comprising a BrdU-labeled polynucleotide as set forth above, wherein the polynucleotide binds to the nucleic acid analyte;

washing the sample;

contacting the sample with an anti-BrdU antibody conjugated to a detectable moiety or to an enzyme; and detecting the detectable moiety or enzyme.

The method as set forth above may further comprise fixing the sample prior to incubating the sample. Methods for fixing cells for in-situ analysis are well-known in the art (See, for example, Sambrook et al., Molecular Cloning, A Laboratory Manual," 3rd Ed., Vol. 1, Chapter 7, Protocol 9, sections 7.46 to 7.50 and Ausubel et al., Current Protocols in Molecular Biology, Vol. 2, Chapter 14, In Situ Hybridization and Immunohistochemistry). Non-limiting examples of fixing include, but are not limited to, contacting the sample with an acid or a cross-linking agent.

A composition is also provided which comprises: adenosine triphosphate (ATP); uridine triphosphate (UTP); guanosine triphosphate (GTP); cytidine triphosphate (CTP); and a compound of the formula:

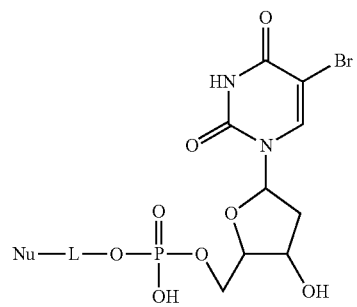

wherein "Nu" is a ribonucleotide triphosphate and wherein L is a linker group. In some embodiments, a kit is also provided which comprises a composition as set forth above and an RNA polymerase.

In some embodiments, a composition is also provided which comprises 2' deoxy adenosine triphosphate (dATP); 2' deoxy guanosine triphosphate (dGTP); 2' deoxy cytidine triphosphate (dCTP); and thymidine triphosphate (dTTP) and a compound of the formula:

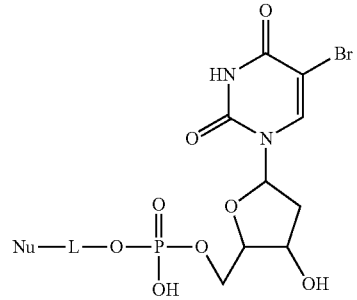

wherein "Nu" is a 2'-deoxyribonucleotide triphosphate and wherein L is a linker group. In some embodiments, a kit is also provided which comprises a composition as set forth above and a DNA polymerase.

Materials and Methods

Reagents

All the reagents and solvents are used as such without further purification, unless otherwise stated. 5'-Dimethoxytrityl-5-bromo-2'-deoxy Uridine, 2'-succinoyl-long chain alkylamine-CPG (5-Br-dU-CPG) and 10-carboxy-decyl-(2-cyanoethyl)-(N,N-diisopropyl)-phosphoramidite, N-hydroxysuccinimide ester were purchased from Glen Research, USA. 5-[3-Aminoallyl]uridine 5'-triphosphate, and 5-[3-Aminoallyl] 2'-deoxy uridine 5'-triphosphate were obtained from Ambion. The detritylation reagent (3% trichloroacetic acid in dichloromethane), activator (i.e. 5-Ethylthio-1H-tetrazole in anhydrous acetonitrile), oxidizing solution {i.e. 0.05M $I_2$ in THF/$H_2$O/Pyridine (7:2:1)}, and acetonitrile were obtained from Glen Research, USA. 50 mM Sodium borate buffer at a pH of 8.5 was obtained from Ambion. Air tight glass syringes were obtained from VWR. The probes ware analyzed by Mass Spectroscopy (i.e., LC/MS (ABI), and by analytical HPLC (Aliance, Water's) using Hypersil SAX columns, 5 μm, 250×4.6 mm (Altech).

Solid Phase Synthesis of BrdU-rUTP and BrdU-dUTP Probes

BrdU-rUTP and BrdU-dUTP probes were synthesized on long chain alkylamine controlled pore glass support (80-100 mesh, 500° A) by using a 5' carboxy modifier {i.e. 10-Carboxy-decyl-(2-cyanoethyl)-(N,N-diisopropyl)-phosphoramidite, N-hydroxysuccinimide ester} following conventional protocols (see, for example, Tanaka et al., Nucleic Acid Res., 10, 3240, 1982). 5' coupling was achieved manually using a syringe technique (see, for example, Murakami et al., Nucleic Acids Res., 19, 4097, 1991). The bioconjugation of N-hydroxysuccinimide ester bearing from 5'-BrdU CPG and 5-[3-aminoallyl]uridine 5'-triphosphate/5-[3-aminoallyl]2'-deoxy uridine 5'-triphosphate was achieved in 50 mM sodium borate buffer pH 8.5 at room temperature for 3 hours.

The 5'-DMT-BrdU loaded CPG, 66 μmol/g (0.5 gm, 33.03 μmol) was poured into a 50 mL gas tight syringe with a glass wool plug at the inlet. The support was washed initially with anhydrous $CH_3CN$ (4×35 mL). The 5'-dimethoxytrityl (DMT) protecting group was then removed by washing with 3% trichloroacetic acid in dichloromethane (5×40 mL, 5 min). The support was then washed with anhydrous $CH_3CN$ (4×40 mL). The coupling of 10-carboxy-decyl-(2-cyanoethyl)-(N,N-diisopropyl)-phosphoramidite, N-hydroxysuccinimide ester solution (20 mL, 0.1M solution in $CH_3CN$) was drawn into the syringe followed by 5-ethylthio-1H-tetrazole activator in anhydrous acetonitrile solution (20 mL, 0.3 M in $CH_3CN$). It was agitated for 20 min and the solution was ejected. The support was then washed with anhydrous $CH_3CN$ (4×40 mL) and oxidized with a (0.05M, 40 mL) $I_2$ in $THF/H_2O/Pyridine$ (7:2:1) for 20 min. The support was then washed with anhydrous acetonitrile (5×40 mL), until no more brown color was observed coming from the support.

Figure 2:
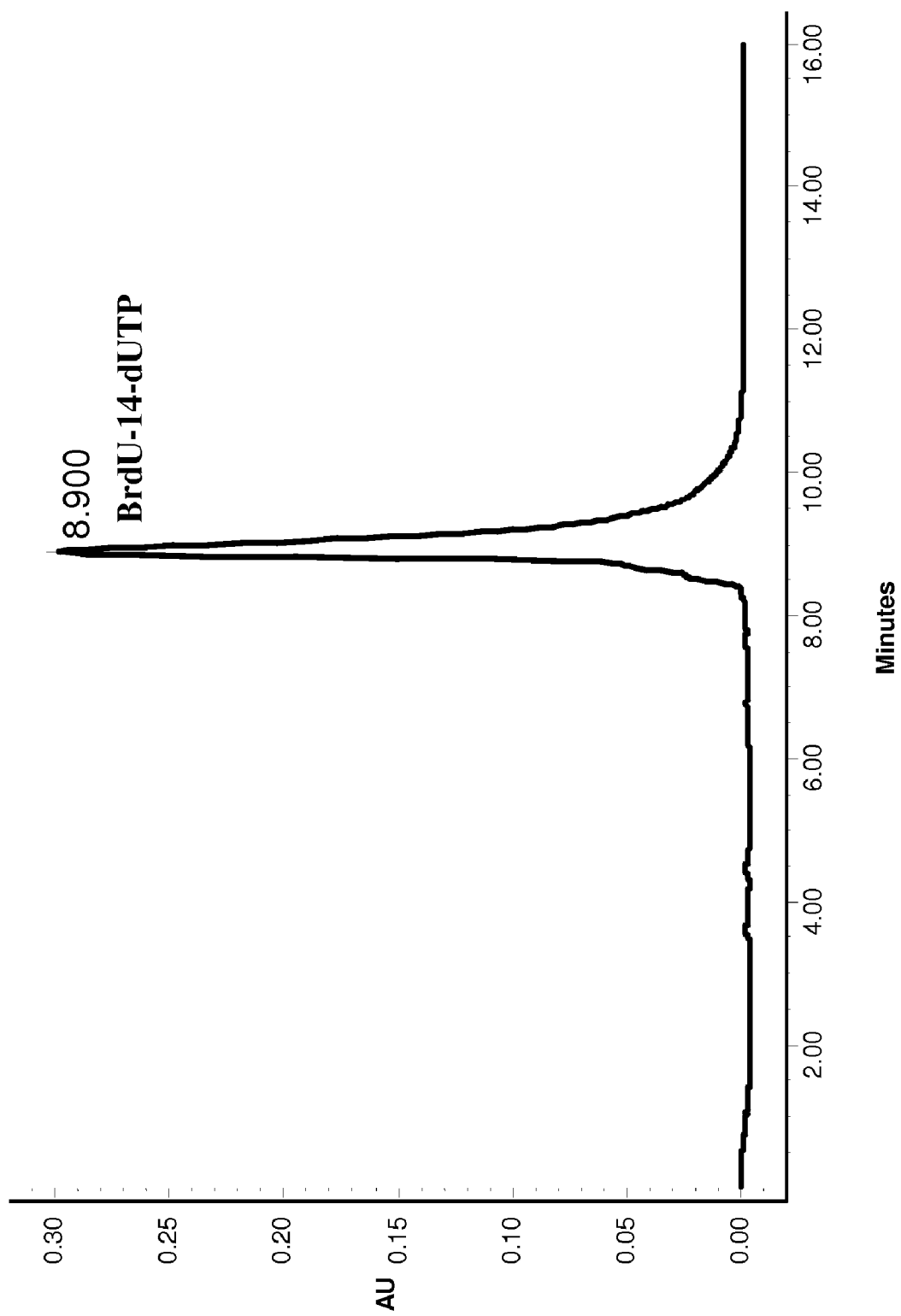
FIG. 2 is an HPLC Profile of a 5-bromo-2'-deoxy-uridine (BrdU) labeled 2'-deoxy uridine triphosphate (dUTP) probe.

Then support was air-dried and transferred into a vial containing 5 mL of 50 mM sodium borate buffer pH 8.5. To this, a solution of 5-[3-aminoallyl]uridine 5'-triphosphate or 5-[3-aminoallyl]2'-deoxy uridine 5'-triphosphate (3 mL, 0.25M) in sodium borate buffer at a pH of 8.5 was added. The reaction mixture was slowly agitated for 4 hours at room temperature. After 4 hours, the supernatant was taken out from the support and washed with distilled water (6×15 mL) in order to remove any traces of aminoallyl UTP or aminoallyl dUTP. Then the support was washed with anhydrous acetonitrile (2×15 mL) and air-dried. The support was transferred into a capped vial and treated with concentrated methanolic $NH_4OH$ 1:4 ratio of (20 mL) for 3 hours at 55° C. temperature in water bath. After removal of ammonia under nitrogen current, the supernatant was taken from the support. The support was washed twice with distilled water (2×6 mL). The aqueous layers were combined and lyophilized. The resulting probe was analyzed by Mass Spectroscopy and analytical HPLC. The HPLC profile of the BrdU-rUTP probe is shown in FIG. 1. The HPLC profile of the BrdU-dUTP probe is shown in FIG. 2. The product was confirmed by mass spectrometry.

Determination of Sensitivity of Probes by Blot Hybridization

Dot and slot blotting are techniques for immobilizing several preparations of nucleic acids on the same solid support, usually a charged nylon membrane or nitrocellulose. Blot hybridizations with specific nucleic acid probes can provide information regarding gene expression and genome structure. In order to find out the sensitivity of the BrdU-14-UTP probe, VIP (i.e. vasoactive intestinal polypeptide plasmid) DNA was used. VIP DNA was digested and linearized DNA was used for transcription. Linearized VIP DNA was transcribed by using normal nucleotide triphosphates (NTPs) except UTP and BrdU-14-UTP was used in 1:1 ratio in the presence of T3 RNA polymerase, which gave an antisense strand. In order to obtain a sense strand, the linearized VIP DNA was transcribed by using T7 RNA Polymerase using normal NTPs. Sense and antisense probes were spotted on nitrocellulose membrane with various dilutions. After hybridization, excess probe was washed away and the hybridized probe was reacted by using alkaline phosphatase conjugated anti-bromodeoxyuridine antibodies and detected by using BCIP/NBT color reagents. BCIP refers to 5-Bromo-4-chloro-3-indolylphosphate and NBT refers to nitroblue tetrazolium chloride. A blot hybridization procedure was carried out as per standard protocols (Sambrook et al., Molecular Cloning, A Laboratory Manual, Third Edition, Vol. 1, Chapter 7, protocol 9, section 7.46 to 7.50; and Ausubel et al., Current Protocols in Molecular Biology, Vol. 2, Chapter 14, In Situ Hybridization and Immunohistochemistry). The results indicated that the BrdU-14-UTP probe had good detection sensitivity in a blot hybridization format.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method comprising:
reacting a compound (1) which is bound to a support:

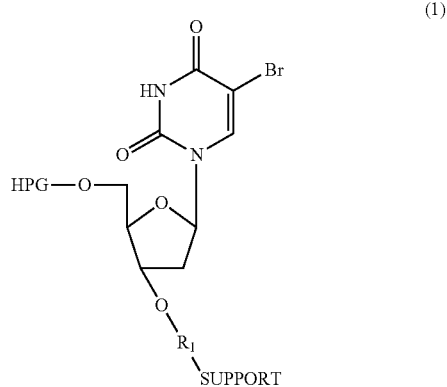

(1)

wherein "$R_1$" is a group linking the nucleoside moiety to the support and "HPG" is a protecting group, with the compound (2):

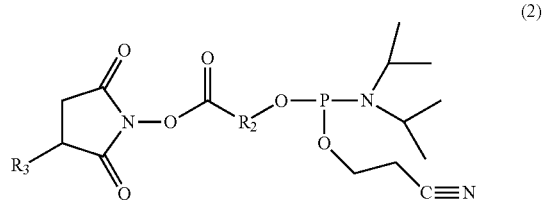

(2)

wherein $R_2$ is a linking group and $R_3$ is H or $SO_3^-$, to form a compound (3):

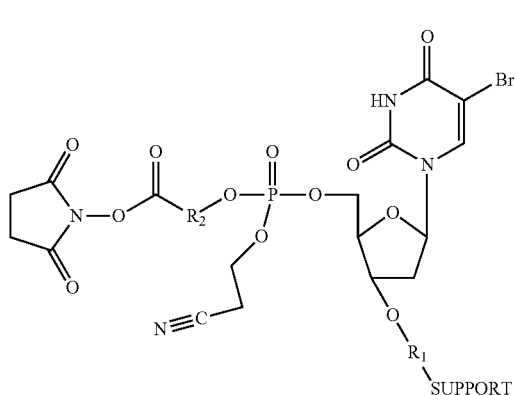
(3)
reacting the compound (3) with the compound (4):
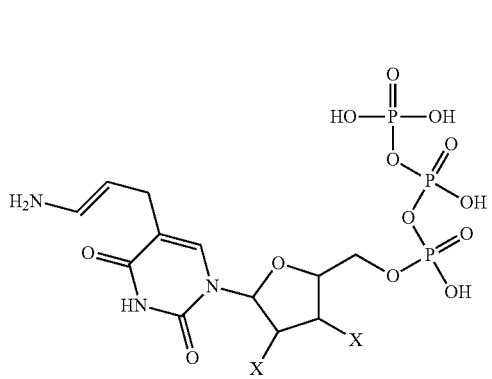
(4)
wherein each X is independently H or OH, to form a compound (5);
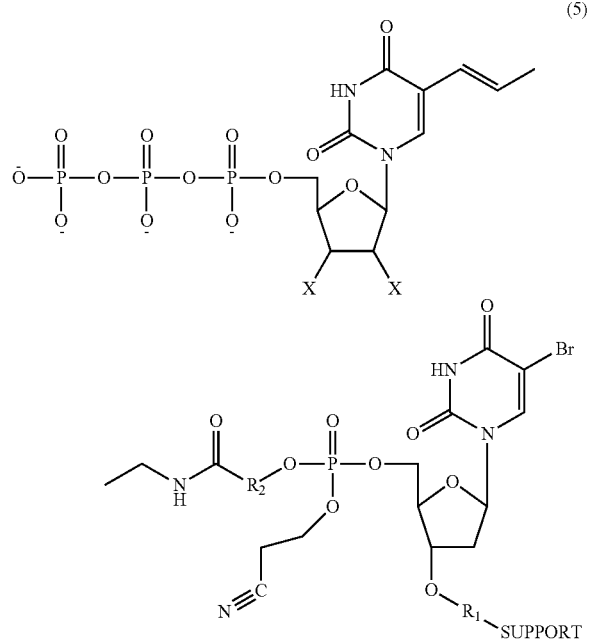
(5)
and removing the compound (5) from the support to form a compound (6);
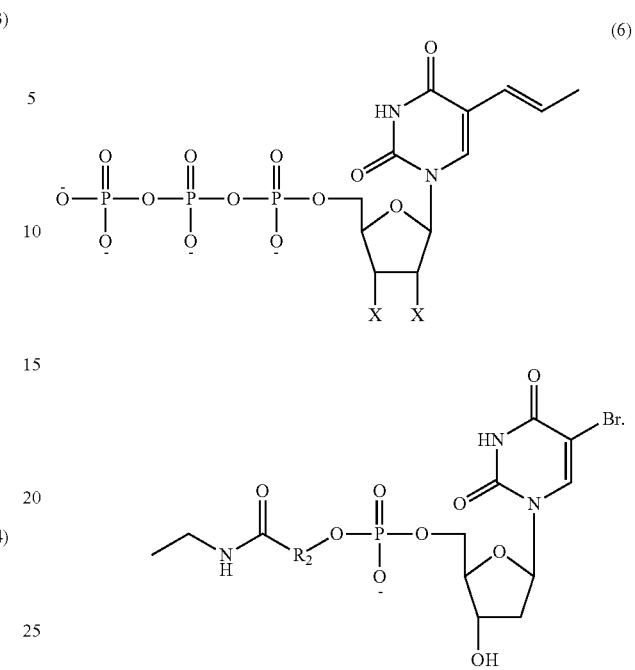
(6)
2. The method of claim 1, wherein $R_2$ is selected from the group consisting of:
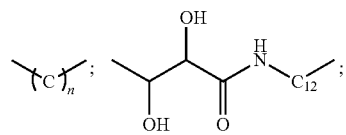
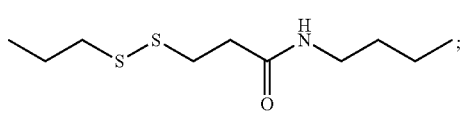
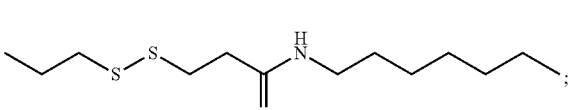
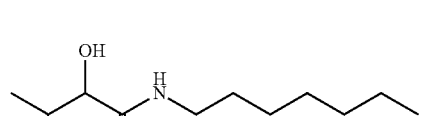
; and

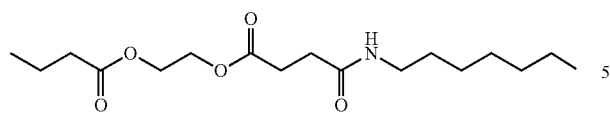
wherein n is an integer of from 6 to 12.
3. The method of claim 1, wherein $R_1$ comprises an amino acid.
4. The method of claim 3, wherein $R_1$ comprises:
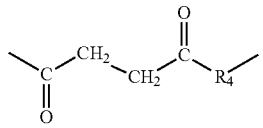
wherein $R_4$ is an amino acid.
5. The method of claim 1, wherein "Y" is a dimethoxytrityl (DMT) group.
* * * * *